United States Patent
Sabbagh et al.

(10) Patent No.: US 8,313,737 B2
(45) Date of Patent: Nov. 20, 2012

(54) HAIR TREATMENT PROCESS FOR SMOOTHING THE HAIR

(75) Inventors: Anne Sabbagh, Rueil Malmaison (FR); Priscille Devin-Baudoin, Vanves (FR)

(73) Assignee: L'Oreal S.A., Paris (FR)

( * ) Notice: Subject to any disclaimer, the term of this patent is extended or adjusted under 35 U.S.C. 154(b) by 1588 days.

(21) Appl. No.: 10/825,154

(22) Filed: Apr. 16, 2004

(65) Prior Publication Data

US 2005/0013786 A1 Jan. 20, 2005

Related U.S. Application Data

(60) Provisional application No. 60/477,363, filed on Jun. 11, 2003.

(30) Foreign Application Priority Data

Apr. 16, 2003 (FR) ...................................... 03 04770

(51) Int. Cl.
*A61K 7/09* (2006.01)
(52) U.S. Cl. ..................................................... 424/70.2
(58) Field of Classification Search ................... 424/70.1
See application file for complete search history.

(56) References Cited

U.S. PATENT DOCUMENTS

| | | |
|---|---|---|
| 4,103,145 A | 7/1978 | Oliveri |
| 4,308,878 A | 1/1982 | Silva |
| 4,956,175 A | 9/1990 | Maignan et al. |
| 5,015,767 A | 5/1991 | Maignan et al. |
| 5,046,516 A | 9/1991 | Barradas |
| 5,085,860 A | 2/1992 | Junino et al. |
| 5,106,612 A | 4/1992 | Maignan et al. |
| 5,334,337 A | 8/1994 | Voelker et al. |
| 5,449,805 A | 9/1995 | Junino et al. |
| 5,466,878 A | 11/1995 | Junino et al. |
| 5,494,058 A | 2/1996 | Chan |
| 5,582,257 A | 12/1996 | Junino et al. |
| 5,957,140 A | 9/1999 | McGee |
| 5,983,903 A | 11/1999 | Nanba et al. |
| 6,076,530 A | 6/2000 | Braida-Valerio et al. |
| 6,303,110 B1 | 10/2001 | Maubru et al. |
| 6,521,219 B1 | 2/2003 | Hirata |
| 6,692,776 B2 | 2/2004 | Hirata |

FOREIGN PATENT DOCUMENTS

| | | |
|---|---|---|
| DE | 197 25 004 | 12/1998 |
| EP | 0 354 835 | 2/1990 |
| EP | 0 368 763 | 5/1990 |
| EP | 0 432 000 | 6/1991 |
| EP | 0 514 282 | 11/1992 |
| EP | 0 669 430 A1 | 3/1996 |
| EP | 0 774 248 A1 | 5/1997 |
| EP | 1 277 459 A1 | 1/2003 |
| FR | 2 679 448 | 1/1993 |
| JP | 9-132515 | 5/1997 |
| JP | 2001-72557 | 3/2001 |
| WO | WO 97/15272 | 5/1997 |
| WO | WO 99/17719 | 4/1999 |
| WO | WO 00/44337 | 8/2000 |
| WO | WO 02/41857 | 5/2002 |

OTHER PUBLICATIONS

Patent Abstract of Japan for JP 2001-072557, published Mar. 21, 2001.
Patent Abstract of Japan for JP 2001-213741, published Aug. 7, 2001.
Patent Abstract of Japan for JP 2002-053428, published Feb. 19, 2002.
Patent Abstract of Japan for JP 2003-055166, published Feb. 26, 2003.
English language Derwent Abstract of EP 0 774 248 A1, May 21, 1997.
English Derwent Abstract for FR 2 679 448.
English Derwent Abstract for EP 0 368 763.
English Abstract for DE 197 25 004, dated Dec. 24, 1998.
Machine Translation of JP 9-132515, dated May 20, 1997.
Notice of Opposition dated Mar. 6, 2008 for European Patent No. 1 468 667 (priority application to the present application).

*Primary Examiner* — Shanon A Foley
(74) *Attorney, Agent, or Firm* — O'Brien Jones PLLC

(57) ABSTRACT

The present disclosure relates to a hair treatment process that comprises applying to the hair a composition comprising at least one ceramide compound in a cosmetically acceptable medium and applying an iron to the hair wherein the iron temperature is at least 60° C. and raises the temperature of the hair. The process may be used for smoothing the hair.

20 Claims, No Drawings

HAIR TREATMENT PROCESS FOR SMOOTHING THE HAIR

This application claims benefit of U.S. Provisional Application No. 60/477,363, filed Jun. 11, 2003.

The present disclosure relates to hair treatment processes for smoothing the hair using a composition comprising at least one ceramide.

The most common technique in the art for permanently reshaping the hair comprises, in a first stage, opening the disulphide —S—S— bonds of keratin (cystine) using a composition comprising a suitable reducing agent, i.e., a reducing step. Next, in a second stage, after the treated hair has been rinsed, the disulphide bonds are reconstituted by applying to the hair, which has been placed under tension beforehand (rollers and the like), an oxidizing composition, i.e., oxidation step, also known as the fixing step. This second step generally gives the hair the desired shape. Further, using this technique, it may be possible to make the hair wavy, or to relax or straighten it. The new shape given to the hair by a chemical treatment, such as above, may be long-lasting and for example, withstand the action of washing with water or shampoo, as opposed to standard techniques of temporary reshaping, such as hairsetting.

The drawbacks of the permanent-waving techniques known to date is that they may cause long-term damage in the quality of the hair. For example, the damage can be a reduction in the hair's cosmetic properties, such as its sheen, and degradation of the hair's mechanical properties, such as degradation of its mechanical strength due to swelling of the hair during the rinsing between the reduction step and the oxidation step, which may also be reflected by an increase in the porosity of the hair. As a result, the hair may be weakened and become brittle during subsequent treatments such as blow-drying.

To reduce the damage to the hair, it is known practice to use conditioners such as silicones, for example, as taught in international patent application WO 99/17719, a dimethicone polyol ester combined with a polypeptide containing silanol end functions, as in international patent application WO 00/44337, or alternatively peptides and/or amino acids, as in international patent application WO 02/41857.

Unfortunately, these conditioners do not entirely eliminate the damage done to the hair and its properties. For example, in the case of permanent-reshaping treatments, the hair may still have an unsatisfactory feel.

The present inventors have now found, surprisingly, that a hair treatment process comprising applying to the hair a composition comprising at least one ceramide compound and heating the hair by applying an iron, for example, a flat or round iron, to the hair, wherein the iron temperature is at least 60° C., affords long-lasting cosmetic properties, for instance excellent smoothing of the hair, tonicity and regeneration of the hair fiber, volumizing (or texturizing) of the fiber, and good disentangling and softness results.

The use of a flat or round iron, for example, helps the at least one ceramide compound to penetrate better into the hair fibers and also increases the composition's remanence with respect to shampooing. The term "iron" as used herein means a heating device that heats the hair and is employed at a temperature of at least 60° C. The portion of the iron that contacts the hair may have different shapes. For instance, it may be chosen from a flat surface ("flat iron") and a rounded surface ("round iron").

One aspect of the present invention is thus a hair treatment process as described below, which also can be used to smooth the hair.

Other characteristics, aspects, and advantages of the disclosure will emerge even more clearly on reading the description and the various examples that follow.

According to the present invention, the hair treatment process comprises applying to the hair a composition comprising at least one ceramide compound in a cosmetically acceptable medium, and then raising the temperature of the hair by applying an iron to the hair wherein the iron temperature is at least 60° C., for example, from 60° to 220° C., and further for example, from 0.1200 to 200° C., this step taking place before or after optionally rinsing the composition from the hair.

In one embodiment, the composition comprising at least one ceramide compound is not rinsed out before treating with the iron.

The at least one ceramide compound may be a compound of formula (I) below:

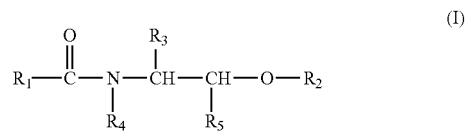

wherein:
R$_1$ is chosen from
saturated and unsaturated, linear and branched C$_9$-C$_{30}$ hydrocarbon radicals, wherein the radicals are optionally substituted with at least one hydroxyl group, the at least one hydroxyl group optionally being esterified with an entity chosen from saturated and unsaturated C$_{16}$-C$_{30}$ fatty acids; and
R"—(NR—CO)—R'— radicals, wherein R is chosen from hydrogen and monohydroxylated and polyhydroxylated, for example, monohydroxylated, C$_1$-C$_{10}$ hydrocarbon radicals, R' and R" are chosen from hydrocarbon radicals in which the sum of the carbon atoms ranges from 9 to 30, and wherein R' is a divalent radical;
R$_2$ is chosen from hydrogen, and (glycosyl)$_n$, (galactosyl)$_m$, and sulphogalactosyl radicals, wherein n is an integer ranging from 1 to 4 and m is an integer ranging from 1 to 8;
R$_3$ is chosen from hydrogen and saturated and unsaturated C$_{16}$-C$_{27}$ hydrocarbon radicals wherein the hydrocarbon radicals are optionally substituted with at least one C$_1$-C$_{14}$ alkyl radical; and R$_3$ may also be chosen from C$_{15}$-C$_{26}$ α-hydroxyalkyl radicals, wherein the hydroxylalkyl radicals may optionally be esterified with a C$_{16}$-C$_{30}$ α-hydroxy acid;
R$_4$ is chosen from hydrogen; saturated and unsaturated C$_{16}$-C$_{27}$ hydrocarbon radicals; and —CH$_2$—CHOH—CH$_2$—O—R$_6$ radicals, wherein R$_6$ is chosen from C$_{10}$-C$_{26}$ hydrocarbon radicals; and
R$_5$ is chosen from hydrogen, and monohydroxylated and polyhydroxylated C$_1$-C$_4$ hydrocarbon radicals.

For example, the at least one ceramide compound used in the process of the present disclosure corresponds to formula (I) wherein R$_1$ is chosen from optionally hydroxylated saturated and unsaturated alkyl radicals of C$_{16}$-C$_{22}$ fatty acids; R$_2$ is hydrogen; and R$_3$ is chosen from optionally hydroxylated saturated linear C$_{15}$ radicals. Further, for example, the at least one ceramide is chosen from:
N-linoleoyldihydrosphingosine,
N-oleoyldihydrosphingosine,
N-palmitoyldihydrosphingosine, N-stearoyldihydrosphingosine,
N-behenoyldihydrosphingosine,
N-2-hydroxypalmitoyldihydrosphingosine, and
N-stearoylphytosphingosine,
and for instance, from N-oleoyidihydrosphingosine, N-2-hydroxypalmitoyldihydrosphingosine, and N-stearoylphytosphingosine.

The at least one ceramide compound is present in an amount ranging from 0.001% to 20% by weight, for example, from 0.01% to 10% by weight and further for example, from 0.1% to 0.5% by weight, relative to the total weight of the composition. In one embodiment, the at least one ceramide compound may be present in an amount of 0.5% by weight, relative to the total weight of the composition.

The cosmetically acceptable medium used in the present disclosure may be water or a water/solvent mixture, such as, for example, an aqueous-alcoholic solution of a $C_{1-4}$ lower alcohol such as ethanol, isopropanol, or butanol.

In the process disclosed herein, the composition comprising at least one ceramide compound may be applied, for example, before or after a reducing composition comprising at least one reducing agent, and the application of this reducing composition may optionally be followed by rinsing.

In another aspect of the process of the disclosure, the composition comprising at least one ceramide further comprises at least one reducing agent.

The reducing agents that may be used in the process are, for example, chosen from those used in processes for permanently reshaping the hair, such as alkali metal sulphites and bisulphites, alkaline-earth metal sulphites and bisulphites, ammonium sulphites and bisulphites, and thiols. In one embodiment, the reducing agent is chosen from thiols. Among these reducing agents, the ones most commonly used are cysteine and its various derivatives such as N-acetylcysteine; cysteamine and its various derivatives (for example, its $C_1$-$C_4$ acyl derivatives such as N-acetylcysteamine or N-propionyl cysteamine); thiolactic acid and its esters (for example, glyceryl monothiolactate); thioglycolic acid and its esters, for example, glyceryl or glycol monothioglycolate, diammonium dithiodiglycolate or ammonium thioglycolate, and thioglycerol. Mention may also be made of the non-limiting examples chosen from: N-mercaptoalkylamides of sugars such as N-(2-mercaptoethyl)gluconamide, β-mercaptopropionic acid and its derivatives; thiomalic acid; pantethine; the N-(mercaptoalkyl)-ω-hydroxyalkyamides described in patent application EP-A-354 835; the N-mono- or N,N-dialkylmercapto-4-butyramides described in patent application EP-A-368 763; the aminomercaptoalkylamides described in patent application EP-A-432 000; the alkylaminomercaptoalkylamides described in patent application EP-A-514 282; and the mixture of 2-hydroxypropyl thioglycolate (2/3) and of 2-hydroxy-1-methylethyl thioglycolate (67/33) described in patent application FR-A-2 679 448.

In one embodiment, the at least one reducing agent may be chosen from thioglycolic acid and its esters, cysteamine and cysteine. In another embodiment, the at least one reducing agent is chosen from thioglycolic acid and its esters, such as, for example, glyceryl or glycol monothioglycolate, ammonium thioglycolate, and cysteine.

The at least one reducing agent is present in an amount ranging from 0.1% to 25% by weight and for example, from 1% to 15% by weight, relative to the total weight of the composition.

The reducing composition that may be used in the process of the present disclosure, for example, has a pH ranging from 5 to 11 and further for example, from 6.5 to 10.

The pH of the reducing compositions may optionally be adjusted by adding acidifying agents, for instance hydrochloric acid, acetic acid, lactic acid or boric acid, or basifying agents such as ammonia, monoethanolamine, or ammonium bicarbonate.

The compositions used in the process according to the dislcosure may also further comprise other ingredients such as linear or cyclic, volatile or non-volatile silicones; cationic polymers; peptides and derivatives thereof; protein hydrolysates; waxes; swelling agents; penetrating agents or agents for reinforcing the efficacy of the reducing agent, such as the $SiO_2$/PDMS (polydimethylsiloxane) mixture; dimethylisosorbitol; urea and its derivatives; pyrrolidone; N-alkylpyrrolidones; thiamorpholinone; alkylene glycol or dialkylene glycol alkyl ethers, for instance propylene glycol monomethyl ether, dipropylene glycol monomethyl ether, ethylene glycol monoethyl ether, and diethylene glycol monoethyl ether; $C_3$-$C_6$ alkanediols, for instance 1,2-propanediol and 1,2-butanediol; 2-imidazolidinone, and also other compounds such as pantothenic acid; anionic, cationic, nonionic, amphoteric or zwitterionic surfactants; agents for preventing hair loss; antidandruff agents; natural or synthetic, associative or non-associative thickeners; suspension agents; sequestering agents; opacifiers; dyes; sunscreens; vitamins or provitamins; fragrances; and preserving agents, and mixtures thereof.

For example, the reducing composition used herein may further comprise at least one cationic agent. The at least one cationic agent is, for example, polymeric. Cationic polymers that may be mentioned include the products known under the INCI names Polyquaternium 10 and Hexadimethrine Chloride.

The composition used in the process disclosed herein may be in the form of a thickened or non-thickened lotion, a cream, a gel, or any other suitable form.

In addition, the process may further comprise using the above-mentioned iron in successive separate touches for a few seconds, by gradual movement, or sliding along locks.

As examples of irons that may be used according to the disclosure, mention may be made of flat or round irons of all types and for example, in a non-limiting manner, those described in U.S. Pat. Nos. 4,103,145, 4,308,878, 5,983,903, 5,957,140, 5,494,058, and 5,046,516.

The process according to the disclosure may further comprise an additional step of pre-drying the hair with a dryer before using the iron, so as to avoid substantial release of steam that might burn the operator's hands, i.e., the hairstylist's hands, and the subject's scalp.

The process according to the present disclosure may also include an additional fixing step that comprises applying an oxidizing composition to the dried hair, i.e., after the iron has been used.

This oxidizing, i.e., fixing, composition comprises at least one oxidizing agent that may be chosen from hydrogen peroxide and aqueous hydrogen peroxide solution, and urea peroxide; alkali metal bromates; persalts such as perborates and persulphates; and enzymes such as peroxidases and 2-electron oxidoreductases. For example, the at least one oxidizing agent may be chosen from hydrogen peroxide and alkali metal bromates.

When present, the concentration of aqueous hydrogen peroxide solution may range from 1 to 10 volumes, for example, ranges from 6 to 8 volumes.

In addition, bromate may be present in an amount ranging from 1% to 12% by weight and the persalt may be present in an amount ranging from 0.1% to 15% by weight, relative to the total weight of the oxidizing composition.

Another subject of the invention is the use of the process of the present invention for smoothing the hair.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLES

Example 1

A smoothing cream having the composition below was prepared, the proportions being expressed as percentages by weight.

| | |
|---|---|
| N-Oleyldihydrosphingosine | 0.5 |
| Ammonium thioglycolate as an aqueous 71% solution | 8 |
| Diammonium dithiodiglycolate as an aqueous 48% solution | 2.5 |
| 2-Octyldodecanol | 2 |
| Ethylenediaminepentaacetic acid, pentasodium salt, as an aqueous 40% solution | 0.4 |
| Cetylstearyl alcohol (50/50) | 8 |
| Aqueous ammonia (20% NH$_3$) | 3.3 |
| Oxyethylenated cetyl alcohol (containing 2 mol of ethylene oxide) | 3 |
| Cetyltrimethylammonium chloride as an aqueous 25% solution | 4 |
| Behenyltrimethylammonium chloride as an 80% solution in water/isopropanol | 4 |
| Cetyl palmitate | 2 |
| Polydimethylsiloxane containing aminoethylaminopropyl and α,ω-silanol groups, as an aqueous 35% cationic emulsion | 2.85 |
| Fragrance | 0.3 |
| Deionized water qs | 100 |

Smoothing operations were performed on 9 asiatic models with colored hair, using the smoothing cream whose composition is given above.

The smoothing cream was applied to clean, wet hair, left in contact with the head of hair for a time that is sufficient to reduce the hair, and was then rinsed out. The hair was then towel-dried, predried using a dryer, and then smoothed lock by lock using a flat iron heated to 180° C. The fixing agent (12-volumes aqueous hydrogen peroxide solution, pH 3) was then applied directly to the dry hair, left in contact with the head of hair so as to fix the given shape, and then rinsed out. The hair was then dried using a dryer.

The relaxing and disentangling were very good on wet hair and on dried hair.

Hair that was smooth from the root to the end and manageable was obtained. The hair was coated, treated, and tonic. This treatment afforded good cosmetic qualities without softening the hair and amplified the smoothing effect.

Example 2

A lotion was prepared from the following compounds in the proportions indicated in percentages by weight:

| | |
|---|---|
| N-Oleyldihydrosphingosine | 0.25 |
| Methyl p-hydroxybenzoate | 0.2 |
| Methylalkylalkylamidoethylimidazolinium methosulphate as a 75% solution in propylene glycol | 4.2 |
| Behenyltrimethylammonium chloride as an 80% solution in water/isopropanol | 1.4 |
| Chlorhexidine hydrochloride | 0.02 |
| Deionized water qs | 100 |

This lotion was applied to hair that had just been relaxed. After pre-drying using a hair dryer, the hair was smoothed lock by lock using a flat iron heated to 180° C. Manageable, tonic hair was thus obtained.

What is claimed is:

1. A process for treating hair comprising
   applying to the hair a composition comprising at least one ceramide compound in a cosmetically acceptable medium,
   applying to the hair a reducing composition comprising at least one reducing agent before or after applying to the hair the composition comprising at least one ceramide compound, and optionally rinsing the hair, and
   raising the temperature of the hair by applying an iron to the hair, wherein the temperature of the iron is at least 60° C.

2. The process according to claim 1, wherein the iron is chosen from flat and round irons.

3. The process according to claim 1, wherein the iron temperature ranges from 60° to 220° C.

4. The process according to claim 3, wherein the iron temperature ranges from 120° to 200° C.

5. The process according to claim 1, further comprising optionally rinsing the hair before or after applying the iron.

6. The process according to claim 1, wherein the at least one ceramide compound is a compound of formula (I):

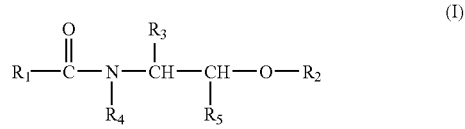

wherein:
—R$_1$ is chosen from
saturated and unsaturated, linear and branched C$_9$-C$_{30}$ hydrocarbon radicals, wherein the radicals are optionally substituted with at least one hydroxyl group, the at least one hydroxyl group optionally being esterified with an entity chosen from saturated and unsaturated C$_{16}$-C$_{30}$ fatty acids; and
R"—(NR—CO)—R'— radicals, wherein R is chosen from hydrogen and monohydroxylated and polyhydroxylated, for example, monohydroxylated, C$_1$-C$_{10}$ hydrocarbon radicals, R' and R" are chosen from hydrocarbon radicals in which the sum of the carbon atoms ranges from 9 to 30, and wherein, R' is a divalent radical;

$R_2$ is chosen from hydrogen, and (glycosyl)$_n$, (galactosyl)$_m$, and sulphogalactosyl radicals, wherein n is an integer ranging from 1 to 4 and m is an integer ranging from 1 to 8;

$R_3$ is chosen from hydrogen and saturated and unsaturated $C_{16}$-$C_{27}$ hydrocarbon radicals wherein the hydrocarbon radicals are optionally substituted with at least one $C_1$-$C_{14}$ alkyl radical; and $R_3$ may also be chosen from $C_{15}$-$C_{26}$ α-hydroxyalkyl radicals, wherein the hydroxylalkyl radicals may optionally be esterified with a $C_{16}$-$C_{30}$ α-hydroxy acid;

$R_4$ is chosen from hydrogen; saturated and unsaturated $C_{16}$-$C_{27}$ hydrocarbon radicals; and —CH$_2$—CHOH—CH$_2$—O—R$_6$ radicals, wherein $R_6$ is chosen from $C_{10}$-$C_{26}$ hydrocarbon radicals; and $R_5$ is chosen from hydrogen, and monohydroxylated and polyhydroxylated $C_1$-$C_4$ hydrocarbon radicals.

7. The process according to claim 6, wherein $R_1$ is chosen from optionally hydroxylated saturated and unsaturated alkyl radicals of $C_{16}$-$C_{22}$ fatty acids; $R_2$ is hydrogen; and $R_3$ is chosen from optionally hydroxylated saturated linear $C_{15}$ radicals.

8. The process according to claim 7, wherein the at least one ceramide compound is chosen from:
N-linoleoyldihydrosphingosine,
N-oleoyldihydrosphingosine,
N-palmitoyldihydrosphingosine,
N-stearoyldihydrosphingosine,
N-behenoyldihydrosphingosine,
N-2-hydroxypalmitoyldihydrosphingosine, and
N-stearoylphytosphingosine.

9. The process according to claim 8, wherein the at least one ceramide compound is chosen from N-oleoyldihydrosphingosine, N-2-hydroxypalmitoyldihydrosphingosine, and N-stearoylphytosphingosine.

10. The process according to claim 1, wherein the at least one ceramide compound is present in an amount ranging from 0.001% to 20% by weight, relative to the total weight of the composition.

11. The process according to claim 10, wherein the at least one ceramide compound is present in an amount ranging from 0.01% to 10% by weight, relative to the total weight of the composition.

12. The process according to claim 11, wherein the at least one ceramide compound is present in an amount ranging from 0.1% to 5% by weight, relative to the total weight of the composition.

13. The process according to claim 1, wherein the reducing composition has a pH ranging from 5 to 11.

14. The process according to claim 13, wherein the reducing composition has a pH ranging from 6.5 to 10.

15. The process according to claim 1, wherein the at least one reducing agent is chosen from thioglycolic acid and its esters, cysteamine, and cysteine.

16. The process according to claim 15, wherein the at least one reducing agent is chosen from thioglycolic acid, glyceryl monothioglycolate, glycol monothioglycolate, ammonium thioglycoloate, and cysteine.

17. The process according to claim 1, further comprising applying an oxidizing composition to dry hair after applying the iron to the hair.

18. A process for smoothing hair comprising
applying to the hair a composition comprising at least one ceramide compound in a cosmetically acceptable medium,
applying to the hair a reducing composition comprising at least one reducing agent before or after applying to the hair the composition comprising at least one ceramide compound, and optionally rinsing the hair, and
smoothing the hair by applying an iron to the hair, wherein the temperature of the iron is at least 60° C.

19. The process according to claim 1, further comprising pre-drying the hair with a dryer before applying the iron.

20. The process according to claim 18, further comprising pre-drying the hair with a dryer before applying the iron.

* * * * *